United States Patent [19]

Alder

[11] Patent Number: 4,883,877
[45] Date of Patent: Nov. 28, 1989

[54] AZABICYCLOHEPTANES AND PROCESS FOR THEIR PREPARATION

[75] Inventor: Alex Alder, Arisdorf, Switzerland

[73] Assignee: Ciba-Geigy Corporation, Ardsley, N.Y.

[21] Appl. No.: 264,584

[22] Filed: Oct. 31, 1988

[30] Foreign Application Priority Data

Nov. 13, 1987 [CH] Switzerland .......................... 4434/87

[51] Int. Cl.$^4$ ............................................ C07D 221/22
[52] U.S. Cl. .................................... 546/112; 546/183
[58] Field of Search ................................. 546/112, 183

[56] References Cited

U.S. PATENT DOCUMENTS 4,797,406  1/1989  Richardson et al. ........... 546/112 X
4,808,718  2/1989  Hartman et al. ................ 546/112 X

OTHER PUBLICATIONS

Oppolzer et al., Ch. Abs. 84(3):17084n, 1976.
Alder, Helv. Ch. Act. 65(8), 1982, p. 2413.
Alder, J. Am. Ch. Soc. 105, p. 6712, 1983.

*Primary Examiner*—Mary C. Lee
*Assistant Examiner*—E. Brendan Magrab
*Attorney, Agent, or Firm*—Stephen V. O'Brien

[57] ABSTRACT

Compounds of the formula I

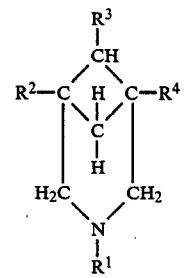

in which $R^1$, $R^2$, $R^3$ and $R^4$ are, for example, H, alkyl, cycloalkyl, aryl or alkaryl are suitable as an ammonium salt-forming component for acid pharmaceutical active ingredients, and in particular for the preparation of azabicyclo[3.1.1.]heptane-substituted alkanediphosphonic acids for the treatment of diseases which can be attributed to disturbances in calcium metabolism.

11 Claims, No Drawings

AZABICYCLOHEPTANES AND PROCESS FOR THEIR PREPARATION

The invention relates to substituted 3-azabicyclo-[3.1.1]heptanes and a process for their preparation by reduction of 3-azabicyclo[3.1.1]heptane-2,4-diones.

The invention relates to compounds of the formula I

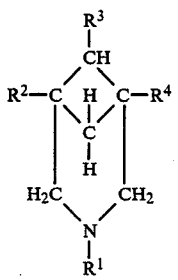

and their ammonium salts, in which $R_1$ is a hydrogen atom, linear or branched $C_1$-$C_{20}$alkyl, $C_3$-$C_8$cycloalkyl, $C_4$-$C_{20}$alkylcycloalkyl, $C_4$-$C_{12}$ cycloalkylalkyl, $C_5$-$C_{20}$alkylcycloalkylalkyl, $C_6$-$C_{14}$aryl, $C_7$-$C_{20}$alkaryl or aralkyl or $C_8$-$C_{20}$alkaralkyl, which is unsubstituted or substituted by halogen, —OH, —CN, —NO$_2$, $C_1$-$C_6$- halogenoalkyl, —COOH, —SO$_3$H, $R^5$CO—, $R^5$COO—, $R^5$OCO—, $R^5$OSO$_2$—, $R^5$SO$_2$—, $R^5$SO$_3$—, $C_1$-$C_6$-halogenoalkyl, $C_1$-$C_6$alkoxy, $C_1$-$C_6$alkylthio, $C_6$-$C_{10}$aryloxy or arylthio or $C_7$-$C_{12}$aralkyloxy or aralkylthio, in which $R^5$ is $C_1$-$C_{12}$-alkyl, $C_4$-$C_7$cycloalkyl, $C_5$-$C_{16}$alkylcycloalkyl or cycloalkylalkyl, $C_6$-$C_{16}$-alkylcycloalkylalkyl, $C_6$-$C_{10}$aryl, $C_7$-$C_{16}$aralkyl or alkaryl or $C_8$-$C_{16}$alkaralkyl, $R^2$ is a hydrogen atom, linear or branched $C_1$-$C_{20}$-alkyl, alkoxy, alkylthio, $C_3$-$C_8$cycloalkyl, $C_4$-$C_{20}$alkylcycloalkyl or cycloalkylalkyl, $C_5$-$C_{20}$alkylcycloalkylalkyl, $C_3$-$C_8$cycloalkyloxy or -thio, $C_4$-$C_{20}$alkylcycloalkyloxy or —thio or cycloalkylalkyloxy or -thio, $C_5$-$C_{20}$alkylcycloalkylalkyloxy or —thio, $C_6$-$C_{14}$aryl, aryloxy or arylthio, $C_7$-$C_{20}$alkaryl, alkaryloxy or alkarylthio, $C_7$-$C_{20}$aralkyl, $C_7$-$C_{20}$-aralkyloxy or -thio, $C_8$-$C_{20}$alkaralkyl or $C_8$-$C_{20}$alkaralkyloxy or -thio, which is unsubstituted or is substituted as defined for $R_1$, $R^4$ independently has the same meaning as $R^2$, with the exception of $C_6$-$C_{14}$aryl and $C_7$-$C_{20}$alkaryl which is unsubstituted or substituted as defined for $R^1$, and $R^3$ independently has the meaning of $R^2$, or is halogen, carboxyl or carboxylate having 2 to 16 C atoms, with the proviso that $R^1$, $R^2$, $R^3$ and $R^4$ are not simultaneously H.

$R^1$, $R^2$, $R^3$ and $R^4$ can be substituted by one or more substituents, preferably by one to five, in particular one to three and especially one or two substituents. Suitable substituents are, for example: halogen, in particular F, Cl and Br; —OH, —CN, —NO$_2$, —COOH and —SO$_3$H; $R^5$CO—, $R^5$COO—, $R^5$OCO—, $R^5$SO$_2$—, $R^5$SO$_2$— and $R^5$SO$_3$—, in which $R^5$ is preferably linear or branched $C_1$-$C_6$-, in particular $C_1$-$C_4$alkyl, cyclohexyl, phenyl, $C_1$-$C_4$alkylphenyl, benzyl or $C_1$-$C_4$alkylbenzyl; $C_1$-$C_6$—, preferably $C_1$-$C_4$halogenoalkyl, in which the halogen is, in particular, F or Cl, for example chloromethyl, fluoromethyl, trifluoromethyl, 2-fluoroethyl, 2-chloroethyl, 1,1-difluoroeth-1-yl and 2,2,2-trifluoroeth-1-yl; $C_1$-$C_6$-, preferably $C_1$-$C_4$alkoxy or —alkylthio, for example methoxy, ethoxy, propyloxy, butyloxy, methylthio and ethylthio; $C_6$-$C_{10}$—aryloxy or —arylthio, in particular phenoxy and phenylthio; and $C_7$-$C_{12}$aralkyloxy or —aralkylthio, in particular benzyloxy·or benzylthio.

The hydrocarbon radicals of the substituents can in turn be substituted by one or more, in particular one or two substituents, for example by $C_1$-$C_4$alkyl or —alkoxy, F, Cl, Br, —OH or —CN.

$R^1$, $R^2$, $R^3$ and $R^4$ can be linear or branched alkyl having preferably 1 to 12, in particular 1 to 6 C atoms. Examples are methyl, ethyl and the isomers of propyl, butyl, pentyl, hexyl, heptyl, octyl, nonyl, decyl, undecyl, dodecyl, tetradecyl, hexadecyl, octadecyl and eicosyl.

$R^1$, $R^2$, $R^3$ and $R^4$ can be cycloalkyl having preferably 5 to 7, in particular 5 or 6, ring C atoms, for example cyclopentyl and cyclohexyl.

$R^1$, $R^2$, $R^3$ and $R^4$ can be alkylcycloalkyl or —cycloalkylalkyl with preferably 6 to 16 C atoms. The cycloalkyl radical is preferably cyclopentyl or cyclohexyl. $C_1$-$C_4$Alkylcycloalkyl, for example methyl— or ethylcyclohexyl, and cycloalkylmethyl, for example cyclohexylmethyl, are particularly preferred.

$R^1$, $R^2$, $R^3$ and $R^4$ can be alkylcycloalkylalkyl having preferably 7 to 16 C atoms. The cycloalkyl radical preferably contains 5 or 6 ring C atoms. $C_1$-$C_4$Alkylcycloalkylmethyl, for example (methylcyclohexyl)methyl or (ethylcyclohexyl)methyl, is particularly preferred.

$R^1$, $R^2$ and $R^3$ can be $C_6$-$C_{14}$, in particular $C_6$-$C_{10}$ aryl or $C_7$-$C_{20}$—, preferably $C_7$-$C_{16}$alkaryl. The aryl radical is preferably a naphthyl or, in particular, phenyl radical. Phenyl and $C_1$-$C_4$alkylphenyl are particularly preferred. $R^1$, $R^2$, $R^3$ and $R^4$ can be $C_7$-$C_{20}$-, preferably $C_7$-$C_{16}$aralkyl, or $C_8$-$C_{20}$—, preferably $C_8$-$C_{16}$alkaralkyl. The aryl radical is preferably naphthyl or, in particular, phenyl. Phenyl—$C_nH_{2n}$— and $C_1$-$C_4$alkylphenyl-$C_nH_{2n}$—, in which n is a number from 1 to 4, in particular 1 or 2, are particularly preferred. Benzyl and $C_1$-$C_4$-alkylbenzyl are preferred.

If $R^2$, $R^3$ and $R^4$ are oxy or thio radicals, the same preferred meanings apply to these radicals as to the corresponding hydrocarbon radicals.

$R^3$ can also be halogen, in particular F, Cl or Br, and carboxyl or $C_2$-$C_{16}$—, in particular $C_2$-$C_8$carboxylate. Carboxylate is, in particular, —COO—$C_1$—$C_4$alkyl.

The ammonium salts are, in particular, ammonium hydrosalts of mineral acids and organic acids. Such acids are, for example, hydrogen halide acids (hydrochloric acid, hydrobromic acid or hydroiodic acid), carbonic acid, sulfuric acid, phosphoric acid, $C_1$-$C_8$carboxylic acids (formic acid, acetic acid, propionic acid, trichloro— or trifluoroacetic acid, benzoic acid or phenylacetic acid) and $C_1$-$C_8$sulfonic acids (methanesulfonic acid, trifluoromethanesulfonic acid, phenylsulfonic acid and ptoluenesulfonic acid).

In a preferred embodiment, $R^1$ is a hydrogen atom or unsubstituted or substituted $C_1$-$C_{12}$alkyl, $C_5$-$C_7$cycloalkyl, $C_6$-$C_{16}$alkylcycloalkyl or —cycloalkylalkyl, $C_7$-$C_{16}$alkylcycloalkylalkyl, $C_6$-$C_{10}$aryl, $C_7$-$C_{16}$aralkyl or —alkaryl or $C_8$-$C_{16}$alkaralkyl.

In another preferred embodiment, $R^1$ is a hydrogen atom or unsubstituted or substituted $C_1$-$C_6$alkyl, cyclopentyl, cyclohexyl, $C_1$-$C_4$alkylcyclopentyl or -cyclohexyl, cyclopentyl-$C_nH_{2n}$— or cyclohexyl—$C_nH_{2n}$-, $C_1$-$C_4$alkylcyclopentyl-$C_nH_{2n}$— or $C_1$-$C_4$alkylcyclohexyl-$C_nH_{2n}$-, —, phenyl, $C_1$-$C_4$alkylphenyl, phenyl—$C_nH_{2n}$— or $C_1$-$C_4$alkylphenyl—$C_nH_{2n}$, in which n is a number from 1 to 4, in particular 1 or 2.

$R^1$ is particularly preferably H, unsubstituted or substituted $C_1$-$C_6$-alkyl, phenyl or benzyl.

In another embodiment, $R^2$ is H or unsubstituted or substituted $C_1$-$C_{12}$-alkyl, -alkoxy or -alkylthio, $C_5$-$C_7$-cycloalkyl, $C_6$-$C_{16}$alkylcycloalkyl or -cycloalkylalkyl, $C_7$-$C_{16}$alkylcycloalkylalkyl, $C_5$-$C_7$cycloalkoxy or -thio, $C_6$-$C_{16}$alkylcycloalkyloxy or -thio or -cycloalkylalkyloxy or -thio, $C_7$-$C_{16}$alkylcycloalkylalkyloxy or -thio, $C_6$-$C_{10}$aryl, -aryloxy or -arylthio, $C_7$-$C_{16}$alkaryl, -alkaryloxy or -thio or -aralkyloxy or -thio, $C_8$-$C_{16}$alkaralkyloxy or -thio, $C_7$-$C_{16}$alkaryl or $C_8$-$C_{16}$alkaralkyl. $R^4$ has the same preferred meanings, with the exception of aryl and alkaryl.

In another preferred embodiment, $R^2$ is H or unsubstituted or substituted $C_1$-$C_6$-, in particular $C_1$-$C_4$alkyl, phenyl or $C_1$-$C_4$alkylphenyl. $R^2$ is, in particular, H, $C_1$-$C_4$alkyl or unsubstituted or substituted phenyl or $C_1$-$C_4$alkylphenyl.

$R^4$ is, in particular, H or $C_1$-$C_6$-, especially $C_1$-$C_4$alkyl.

A preferred embodiment is that in which $R^3$ is H or unsubstituted or substituted $C_1$-$C_{12}$alkyl, -alkoxy or -alkylthio, $C_5$-$C_7$cycloalkyl, $C_6$-$C_{16}$ alkylcycloalkyl or -cycloalkylalkyl, $C_7$-$C_{16}$alkylcycloalkylalkyl, $C_5$-$C_7$-cycloalkoxy or -thio, $C_6$-$C_{16}$alkylcycloalkyloxy or -thio or -cycloalkylalkyloxy or -thio, $C_7$-$C_{16}$alkylcycloalkylalkyloxy or -thio, $C_6$-$C_{10}$-aryl, -aryloxy or -arylthio, $C_7$-$C_{16}$alkaryl, -alkaryloxy or -thio or -aralkyloxy or -thio, $C_8$-$C_{16}$alkaralkyloxy or -thio, $C_7$-$C_{16}$-alkaryl or $C_8$-$C_{16}$alkaralkyl, F, Cl, Br, carboxyl or carboxylate having 2 to 8 C atoms.

$R^3$ is particularly preferably H, $C_1$-$C_6$alkyl, unsubstituted or substituted phenyl or $C_1$-$C_4$alkylphenyl.

In a particularly preferred embodiment, $R^4$ is H and $R^2$ is phenyl, or $R^2$ and $R^4$ are methyl and $R^1$ and $R^3$ are H.

The present invention also relates to a process for the preparation of compounds of the formula I, which comprises reducing a compound of the formula II

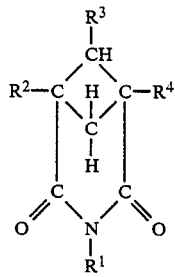
(II)

in which $R^1$, $R^2$, $R^3$ and $R^4$ are as defined in claim 1.

The compounds of the formula II are known in some cases, or they can be prepared analogously to known compounds by photochemical or thermal [2+2]-cycloaddition of N-substituted diacrylimides. Such processes are described, for example, in Helv.Chim.Acta., Vol. 65, Fasc. 8, pages 2405-2412 (1982) and J. of Am. Chem. Soc., Vol. 105, pages 6712-6714 (1983).

The reduction can be carried out electrochemically, catalytically or with metal hydrides. Examples of suitable metal hydrides are LiH, LiAlH$_4$, tributyltin hydride and in particular bisalkoxylated sodium dihydroaluminates. Sodium dihydro-bis-(2-methoxyethoxy)-aluminate is particularly preferred.

The reduction is advantageously carried out in the presence of an inert solvent. Suitable solvents are, for example, ethers (diethyl ether, dibutyl ether, tetrahydrofuran or dioxane) or hydrocarbons, such as, for example, petroleum ether, pentane, methylcyclohexane, benzene, toluene or xylene.

In detail, a procedure can be followed in which the compound of the formula II is taken with the solvent and a solution of the reducing agent is slowly added. The reaction is advantageously carried out under an inert gas atmosphere, for example nitrogen or a noble gas, such as, for example, helium, neon or argon. During the addition of the reducing agent, external cooling may be advantageous, in order to keep the reaction temperature low. When the addition has ended, stirring of the reaction mixture can be continued for some time, if appropriate while heating to the reflux temperature.

To isolate the product, the reaction mixture is advantageously hydrolyzed, for example with aqueous alkali metal hydroxides, the organic phase is separated off, washed and dried and the solvent is distilled off. Purification can be by distillation or by chromatographic methods. It is particularly advantageous to dissolve the cyclic amines of the formula I in an ether, for example diethyl ether, and then to precipitate them as crystalline hydrohalides by passing in a hydrogen halide gas, for example HCl gas, and if appropriate to purify them further by recrystallization.

The amines of the formula I and their salts are suitable as salt-forming components for pharmaceutical active ingredients with acid groups. The compounds according to the invention are particularly suitable for the preparation of medicament active ingredients for the treatment of diseases which can be associated with disturbances in calcium metabolism. These active ingredients can have the formula A

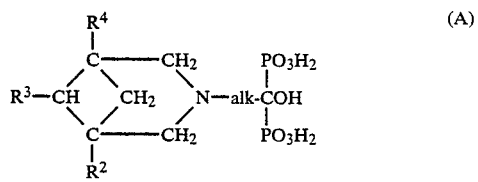
(A)

and salts, for example the disodium salt, can also be used. Alk in this formula ca be alkylene having preferably 2 to 6 C atoms. These compounds can be prepared, for example, by reacting a compound of the formula B

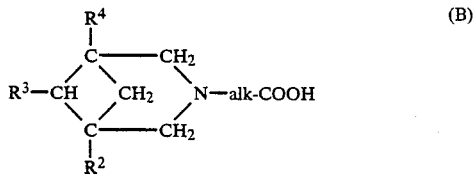
(B)

or the hydrochloride thereof, with concentrated phosphoric acid and phosphorus trichloride, subsequently treating the mixture with hydrochloric acid and then isolating the compounds of the formula (A). The compounds of the formula (B) can be obtained by adding a compound of the formula I in which $R^1$ is H onto olefinically unsaturated aliphatic carboxylic acid esters and hydrolyzing the resulting ester.

The compounds of the formula A and their salts have useful pharmacological properties. In particular, they have a pronounced regulatory action on the calcium metabolism of warm-blooded animals. In particular they effect pronounced inhibition of bone resorption in rats, which can be demonstrated both in te experimental design according to Acta Endocrinol. 78, 613-24 (1975) with the aid of the PTH-induced increase in the serum calcium level following subcutaneous administration in doses of about 0.01 to about 1.0 mg/kg, and in the TPTX (thyroparathyroid-ectomized) rat model with the aid of the experimental hypercalcaemia induced by vitamin $D_3$, following administration of doses of about 0.001 to 1.0 mg subcutaneously. The tumour hypercalcaemia induced by Walker-256 tumours is also inhibited following peroral administration of about 1.0 to about 100 mg/kg. In doses of about 0.01 to 1.0 mg/kg subcutaneously, they furthermore show a distinct inhibition of the progress of chronic arthritic processes in adjuvant arthritis of the rat in the experimental design according to Newbould, Brit. J. Pharmacology 21, 127 (1963) and according to Kaibara et al., J. Exp. Med. 159, 1388-96 (1984).

The following examples illustrate the invention in more detail.

EXAMPLE 1

(a) 1-Phenyl-3-azabicyclo[3.1.1]heptane hydrochloride 25.5 ml of a toluene solution of sodium dihydro-bis-(2-methoxyethoxy)aluminate (70%; FLUKA) are added dropwise to a stirred suspension of 3 g of 1-phenyl-3-azabicyclo[3.1.1]heptane-2,4-dione in 150 ml of toluene under a nitrogen atmosphere. During the addition, the temperature is kept in the range from 25 to 35° C. by external cooling in an ice bath. When the addition has ended, the mixture is subsequently stirred at room temperature (RT) for 15 minutes and is then heated under reflux for 1 hour. After cooling in an ice bath, 25.5 ml of concentrated sodium hydroxide solution are added at 10-15° C. The organic phase is decanted off and the aqueous phase is washed with toluene. The combined organic phases are washed with two portions of 100 ml of water and one portion of 70 ml of brine. After addition of magnesium sulfate, the organic phase is filtered and concentrated under a waterpump vacuum. The brownish oil is dissolved in 50 ml of absolute diethyl ether. The title compound is obtained as a crystalline product by passing in HCl gas, and after filtration with suction is suspended again in diethyl ether, filtered off with suction again and finally dried overnight under a high vacuum. White crystals of melting point (m.p.) 248-249° C. are obtained.

Preparation of the starting material:

(b) 1-Phenyl-3-azabicyclo[3.1.1]heptane-2,4-dione

A solution of 344 g of cerium(IV) ammonium nitrate in 1.1 l of acetonitrile is added dropwise to a stirred solution of 53 g of 3-(4-methoxybenzyl)-1-phenyl-3-azabicyclo[3.1.1]heptane-2,4-dione in 560 ml of acetonitrile at room temperature. After 1 hour, 515 ml of water are added and the mixture is stirred for 2 hours. It is concentrated to half the volume by distilling off the acetonitrile and is then diluted with 1 l of water. The product which has precipitated is filtered off with suction, washed with water and dried in vacuo. The brown-yellowish crystalline substance is taken up in 800 ml of methylene chloride, 11 ml of n-propylamine are added and the mixture is left to stand overnight. The black solution is concentrated and 80 ml of methylene chloridediethyl ether (1:1) are added to the brown crystalline mass, and the crystals are filtered off with suction and dried under a high vacuum. The title compound is obtained as white crystals of m.p. 217-218° C.

(c) 3-(4-Methoxybenzyl)-1-phenyl-3-azabicyclo[3.1.1]heptane-2,4-dione

A solution of 65.7 g of 4-aza-4-(4-methoxybenzyl)-2-phenyl-1,6-hepta-diene-3,5-dione and 0.5 g of 2,6-di-tert-butyl-p-cresol in 1 l of 1,3-dichlorobenzene is stirred at 170° C. for 6 hours. After evaporation, the residue is chromatographed with toluenediethyl ether (9:1) on 2.5 kg of silica gel 60. The brown oil thus obtained is dissolved in 550 ml of diisopropyl ether at 70° C. and cooled in an ice bath, while stirring. The precipitate is filtered off with suction to give, after drying under a high vacuum, the title compound as white crystals of m.p. 87°-88° C.

(d) 4-Aza-4-(4-methoxybenzyl)-2-phenyl-1,6-heptadiene-3,5-dione

A solution of 103 ml of oxalyl chloride in 400 ml of methylene chloride is added dropwise to a stirred solution of 88.8 g of 2-phenylacrylic acid in 7 ml of dimethylformamide and 1.6 l of methylene chloride at room temperature in the course of 2 1/2 hours. When the addition has ended, the mixture is stirred for a further 2 hours and then evaporated in vacuo. The brown oily product is taken up in 600 ml of diethyl ether, separated off from the tacky residue, filtered over HYFLO-Super-Cel ® and concentrated in vacuo. The brown oil is dissolved in 0.8 l of methylene chloride and the solution is added dropwise to a solution, cooled to 0-5° C., of 95.6 g of N-(4-methoxybenzyl)-acrylamide, 6.43 g of 4-dimethylaminopyridine and 63.1 g of triethylamine in 1 l of methylene chloride. When the addition has ended, the mixture is subsequently stirred at room temperature for 3 hours. After the reaction solution has been evaporated to 250 ml, 1 l of diethyl ether is added. The organic phase is decanted off from the tacky residue. The residue is taken up three times with 500 ml portions of diethyl ether and the organic phase is decanted off each time. The combined organic phases are concentrated to 200 ml and filtered over HYFLO-Super-Cel ®. Concentration gives the title compound as a brown oil (which is immediately reacted further in accordance with 1c)).

EXAMPLE 2

(a) 3-Methyl-1-phenyl-3-azabicyclo[3.1.1]heptane hydrochloride

Analogously to Example 1a), 1 g of 3-methyl-1-phenyl-3-azabicyclo[3.1.1]-heptane-2,4-dione in 25 ml of toluene is reacted with 7.4 ml of a toluene solution of sodium dihydro-bis-(2-methoxyethoxy)-aluminate (70%; FLUKA) and the mixture is worked up with 7.4 ml of concentrated sodium hydroxide solution. m.p. of the title compound: 204-207° C.

Preparation of the starting material:

(b) 3-Methyl-1-phenyl-3-azabicyclo[3.1.1]heptane-2,4-dione

A solution of 50 g of 4-aza-4-methyl-2-phenyl-1,6-heptadiene-3,5-dione, 1.2 g of benzophenone and 0.5 g of 2,6-di-tert-butyl-p-cresol in 2.5 l of methylene chloride-acetone (1:1) is irradiated for 48 hours with a mercury vapour lamp (HPK 125W; Philips) positioned in a water-cooled Pyrex finger. After evaporation, the crude product is chromatographed with tolueneethyl acetate (9:1) on silica gel 60. The crystalline product thus obtained is recrystallized from diisopropyl ether-methylene chloride: m.p. 175-176° C.

(c) 4-Aza-4-methyl-2-phenyl-1,6-heptadiene-3,5-dione

A solution, prepared analogously to 1d), of 2-phenylacrylyl chloride (starting from 61.9 g of 2-phenylacrylic acid, 54.3 g of oxalyl chloride and 4 ml of dimethylformamide in 350 ml of methylene chloride) is added dropwise to a stirred solution, cooled to 0–5° C., of 35.6 g of N-methylacrylamide, 89.3 g of triethylamine and 350 ml of methylene chloride. When the addition has ended, the mixture is stirred overnight at room temperature. After the reaction solution has been evaporated to about 200 ml, about 0.5 l of diethyl ether is added, the mixture is filtered and concentrated and the residue is filtered over Hyflo-Super-Cel ®. After concentration, the product is obtained as a dark orange oil (which is immediately reacted further in accordance with 2b).

EXAMPLE 3

(a)
3-Methyl-1-(4-methylphenyl)-3-azabicyclo[3.1.1]heptane hydrochloride

Analogously to Example 1a), 3.4 g of 3-methyl-1-(4-methylphenyl)-3-azabicyclo[3.1.1]heptane-2,4-dione in 75 ml of toluene are reacted with 14 ml of a toluene solution of sodium dihydro-bis-(2-methoxyethoxy)aluminate (70%; FLUKA) and the mixture is worked up with 14 ml of concentrated sodium hydroxide solution. m.p. of the title compound: 192-193° C.

Preparation of the starting material (b)
3-Methyl-1-(4-methylphenyl)-3-azabicyclo[3.1.1]heptane-2,4-dione A solution of 19.9 g of 4-aza-4-methyl-2-(4-methylphenyl)-1,6-heptadiene3,5-dione and 0.2 g of 2,6-di-tert-butyl-p-cresol in 0.5 l of xylene is stirred under reflux for 19 hours. After the reaction mixture has been concentrated, the residue is dissolved in 0.8 l of hot diisopropyl ether, the solution is filtered and the filtrate is concentrated to half. On cooling to room temperature, the title compound is obtained as pale yellow crystals of m.p. 138°–140° C.

(c)
4-Aza-4-methyl-1-(4-methylphenyl)-1,6-heptadiene-3,5-dione

A solution, prepared analogously to 1d), of 2-(4-methylphenyl)-acrylyl chloride (starting from 25.5 g of 2-(4-methylphenyl)-acrylic acid, 22 g of oxalyl chloride, 2 ml of dimethylformamide and 0.5 g of hydroquinone in 590 ml of methylene chloride) is added dropwise to a stirred solution, cooled to 0-5° C., of 11 g of N-methylacrylamide, 35 g of triethylamine and 125 ml of methylene chloride. When the addition has ended, the mixture is subsequently stirred at room temperature for 24 hours. The concentrated reaction material is filtered with methylene chloride on 800 g of silica gel 60 to give, after concentration, the title compound as a dark orange oil (which is immediately reacted further in accordance with 3b)).

EXAMPLE 4

(a)
1-(4-Chlorophenyl)-3-methyl-3-azabicyclo[3.1.1]heptane hydrochloride

Analogously to Example 1a), 3.9 g of 1-(4-chlorophenyl)-3-methyl-3-azabicyclo[3.1.1]heptane-2,4-dione in 70 ml of toluene are reacted with 25 ml of a toluene solution of sodium dihydro-bis-(2-methoxyethoxy)aluminate (70%; FLUKA) and the mixture is worked up with 25 ml of concentrated sodium hydroxide solution. m.p. of the title compound: 180-182° C.

Preparation of the starting material (b)
1-(4-Chlorophenyl)-3-methyl-3-azabicyclo[3.1.1]heptane-2,4-dione A solution of 28.5 g of 4-aza-2-(4-chlorophenyl)-4-methyl-1,6-heptadiene3,5-dione and 0.25 g of 2,6-di-tert-butyl-p-cresol in 1.25 l of methylene chloride-acetone (1:1) is irradiated for 24 hours analogously to 2b). After concentration, the crude product is chromatographed with toluenediethyl ether (9:1) on silica gel 60. Recrystallization from chloroformdiethyl ether gives the title compound with an m.p. of 155-156° C.

(c)
4-Aza-2-(4-chlorophenyl)-4-methyl-1,6-heptadiene-3,5-dione

A solution, prepared analogously to 1d), of 2-(4-chlorophenyl)-acrylyl chloride (starting from 28.8 g of 2-(4-chlorophenyl)-acrylic acid, 19.9 g of oxalyl chloride and 1.5 ml of dimethylformamide in 750 ml of methylene chloride) is added dropwise to a stirred solution, cooled to 0-5° C., of 12 g of N-methylacrylamide, 31.6 g of triethylamine and 130 ml of methylene chloride. When the addition has ended, the mixture is stirred overnight at room temperature. It is worked up as in 1c) to give the title compound as a brown oil, which is immediately reacted further in accordance with 4b).

EXAMPLE 5

3-(4-Methoxybenzyl)-1-phenyl-3-azabicyclo[3.1.1]heptane hydrochloride

Analogously to Example 1a), 2 g of 3-(4-methoxybenzyl)-1-phenyl-3-azabicyclo[3.1.1]heptane-2,4-dione (for the preparation see Example 1c) in 50 ml of toluene are reacted with 5.5 ml of a toluene solution of sodium dihydro-bis-(2-methoxyethoxy)-aluminate (70%; FLUKA) and the mixture is worked up with 5.5 ml of concentrated sodium hydroxide solution. m.p. of the title compound: 209°–211° C.

EXAMPLE 6

(a) exo-6-(4-Chlorophenyl)-3-azabicyclo[3.1.1]heptane hydrochloride

Analogously to Example 1a), 3.5 g of exo-6-(4-chlorophenyl)-3-azabicyclo[3.1.1]heptane-2,4-dione in 75 ml of toluene are reacted with 24 ml of a toluene solution of sodium dihydro-bis-(2-methoxyethoxy)-aluminate (70%; FLUKA) and the mixture is worked up with 24 ml of concentrated sodium hydroxide solution. m.p. of the title compound: 201°–203° C.

Preparation of the starting material (b) exo-6-(4-Chlorophenyl)-3-azabicyclo[3.1.1]heptane-2,4-dione 60 g of tri-n-butyltin hydride are added to a solution of 58.5 g of exo1-bromo-6-(4-chlorophenyl)-3-azabicyclo[3.1.1]heptane-2,4-dione and 1.9 g of bisazoisobutyronitrile in 1 l of absolute tetrahydrofuran under a nitrogen atmosphere. The reaction solution is heated under reflux for 4 hours and then concentrated in vacuo. The crystalline residue is taken up in cyclohexane, the components are mixed and the product is filtered off with suction and washed with diethyl ether. The title compound is obtained as white crystals of m.p. 182–183° C.

(c) exo-1-Bromo-6-(4-chlorophenyl)-3-azabicyclo[3.1.1]heptane-2,4-dione

A solution of 249 g of cerium(IV) ammonium nitrate in 330 ml of water are added dropwise to a stirred suspension of 52.1 g of exo-1-bromo-6-(4- chlorophenyl)-3-(4-methoxybenzyl)-3-azabicyclo[3.1.1]heptane-2,4-dione in 2.1 l of acetonitrile at room temperature. When the addition has ended, the mixture is stirred at room temperature for a further hour and heated to 40° C., and the solution is allowed to cool again slowly to room temperature and is stirred for a further 3 hours. It is concentrated to one third of the volume and then diluted with 1.6 l of water. The product which has precipitated is filtered off with suction, washed with water, diethyl ether and ethyl acetate and dried in vacuo. The title compound is obtained as yellow crystals of m.p. 231°–232° C.

(d) exo-1-Bromo-6-(4-chlorophenyl)-3-(4-methoxybenzyl)-3-azabicyclo[3.1.1]-heptane-2,4-dione A solution of 111.8 g of 4-aza-2-bromo-7-(4-chlorophenyl)-4-(4-methoxybenzyl)-1,6-heptadiene-3,5-dione and 0.6 g of 2,6-di-tert-butyl-p-cresol in 1.4 l of xylene is heated under reflux for 2 hours. After cooling, the dark brown precipitate is separated off from the black reaction solution, stirred in diethyl ether, filtered off with suction and washed with diethyl ether. Fractional crystallization from acetonitrile gives first the title compound as pale yellow crystals of m.p. 177–180° C. and, as the second product, the diastereomeric compound endo-1-bromo-6-(4-chlorophenyl)-3-(4-methoxybenzyl)-3-azabicyclo[3.1.1]heptane-2,4-dione of m.p. 142.5°–143.5° C.

(e) 4-Aza-2-bromo-7-(4-chlorophenyl)-4-(4-methoxybenzyl)-1,6-heptadiene3,5-dione 131.6 g of N-(4-methoxybenzyl)-4-chlorocinnamide are added to a stirred suspension of 100 g of phosphorus pentachloride in 2 l of benzene, while stirring. The mixture is subsequently stirred at room temperature for 30 minutes and then at 50° C. for 30 minutes. After concentration, the dark brown oil is taken up on 600 ml of toluene, the components are mixed and the mixture is concentrated. The residue is dissolved in 1.2 l of carbon tetrachloride, HYFLO-Super-Cel ® is added, the mixture is filtered, the filtrate is evaporated and the residue is dried in vacuo. The orange crystalline intermediate thus obtained is dissolved in 1.2 l of methylene chloride and the solution is added dropwise to a solution of 430 ml of 1 normal aqueous sodium bicarbonate solution, 6.2 g of tetra-n-butyl-ammonium bromide and 600 ml of water. When the addition has ended, 100 ml of 1 normal sodium bicarbonate solution are added dropwise and stirring is continued for 2 hours. The organic phase is separated off and the aqueous phase is extracted with two portions of methylene chloride. The combined organic phases are dried with magnesium sulfate and concentrated and the crude product is dried under a high vacuum. The title compound is obtained as a dark brown oil and is immediately reacted further in accordance with 2d).

EXAMPLE 7

(a) endo-6-(4-Chlorophenyl)-3-azabicyclo[3.1.1]heptane hydrochloride

Analogously to Example 1a), 5.9 g of endo-6-(4-chlorophenyl)-3-azabi- cyclo-[3.1.1]heptane-2,4-dione in 130 ml of toluene are reacted with 24 ml of a toluene solution of sodium dihydro-bis-(2-methoxyethoxy)aluminate (70%; FLUKA) and the mixture is worked up with 24 ml of concentrated sodium hydroxide solution. The title compound is obtained as white crystals of m.p. 236°–238° C.

Preparation of the starting material (b) endo-6-(4-Chlorophenyl)-3-azabicyclo[3.1.1]heptane-2,4-dione A solution of 280 g of cerium(IV) ammonium nitrate in 390 ml of water is added dropwise to a stirred suspension of 47.7 g of endo-6-(4-chloro- phenyl)-3-(4-methoxybenzyl)-3-azabicyclo[3.1.1]heptane-2,4-dione in 0.5 l of acetonitrile at room temperature. When the addition has ended, the mixture is stirred at room temperature for a further 4 hours, 200 ml of acetonitrile is distilled off from the reaction mixture under a waterpump vacuum and the mixture is then diluted with 800 ml of water. It is stirred in an ice bath for 1 hour, the product is filtered off with suction and the pale yellow crystals thus obtained are washed with water and diethyl ether. The intermediate is dissolved in 1 l of methylene chloride, 6.8 g of n-propylamine are added and the mixture is left to stand overnight. It is then filtered and the pale brown solution is concentrated to 70 ml. The concentrate is diluted with 70 ml of diethyl ether, the product is filtered off with suction and the grey-brown crystalline title compound thus obtained is washed with 50 ml of methylene chloridediethyl ether (1:1); melting point 227°–228° C.

(c) endo-6-(4-Chlorophenyl)-3-(4-methoxybenzyl)-3-azabicyclo[3.1.1]- heptane-2,4-dione 49 g of tri-n-butyltin hydride are added to a solution of 72 g of endo-1- bromo-6-(4-chlorophenyl)-3-(4-methoxybenzyl)-3-azabicyclo[3.1.1]heptane2,4-dione (preparation in 6d)) and 1.65 g of bisazoisobutyronitrile in 1.66 l of absolute tetrahydrofuran under a nitrogen atmosphere. The reaction solution is heated under reflux for 1 hour and then concentrated. The crystals thus obtained are worked up in accordance with 2b) to give the title compound as white crystals of m.p. 156°–158° C.

EXAMPLE 8 exo-6-(4-Chlorophenyl)-3-(4-methoxybenzyl)-3-azabicyclo[3.1.1]heptane hydrochloride Analogously to Example 1a), 4.3 g of exo-6-(4-chlorophenyl)-3-(4-methoxy- benzyl)-3-azabicyclo[3.1.1]heptane-2,4-dione in 100 ml of toluene are reacted with 20.5 ml of a toluene solution of sodium dihydro-bis-(2- methoxyethoxy)-aluminate (70%; FLUKA) and the mixture is worked up with 5 ml of concentrated sodium hydroxide solution. The title compound is obtained as colourless crystals of m.p. 232°–234° C. (decomposition).

Preparation of the starting compounds (b) exo-6-(4-Chlorophenyl)-3-(4-methoxybenzyl)-3-azabicyclo[3.1.1]heptane2,4-dione 30 g of tri-n-butyltin hydride are added to 43.5 g of an approximately 1:1 mixture of exo- and endo-1-bromo-6-(4-chlorophenyl)-3-(4-methoxy- benzyl)-3-azabicyclo[3.1.1]heptane-2,4-dione (see preparation in Example 6d)) and 5 g of bisazoisobutyronitrile in 1 1 of absolute tetrahydrofuran under a nitrogen atmosphere. The reaction solution is heated under reflux for 1 hour and on cooling to room temperature the crystalline exo title compound precipitates out; the product is washed with diethyl ether: m.p. 96° C.

EXAMPLE 9 endo-6-(4-Chlorophenyl)-3-(4-methoxybenzyl)-3-azabicyclo

[3.1.1]heptane hydrochloride (a) Analogously to Example 1a), 2 g of endo-6-(4-chlorophenyl)-3-(4-methoxybenzyl)-3-azabiycyclo[3.1.1]heptane-2,4-dione (see preparation in 7c)) in 50 ml of toluene are reacted with 5 ml of a toluene solution of sodium dihydro-bis-(2-methoxyethoxy)-aluminate (70%; FLUKA) and the mixture is worked up with 5 ml of concentrated sodium hydroxide solution. The title compound is obtained as white crystals of m.p. 196°–198° C. (decomposition).

EXAMPLE 10

1,5-Dimethyl-3-azabicyclo[3.1.1]heptane hydrochloride (a) Analogously to Example 1a), 14 g of 1,5-dimethyl-3-azabicyclo[3.1.1]-heptane-2,4-dione in 300 ml of toluene are reacted with 80 ml of a toluene solution of sodium dihydro-bis-(2-methoxyethoxy)-aluminate (70%; FLUKA) and the mixture is worked up with 80 ml of concentrated sodium hydroxide solution. The title compound is obtained as colourless crystals of m.p. 144.5°–145.5° C.

Preparation of the starting compounds (b) 1,5-Dimethyl-3-azabicyclo[3.1.1]heptane-2,4-dione A solution of 47.6 g of 1,5-dimethyl-3-tert-butyl-3-azabicyclo[3.1.1]-heptane-2,4-dione in 215 ml of trifluoroacetic acid is heated under reflux for 6 hours. The evaporated reaction mixture is taken up in diethyl ether and the product which has precipitated as crystals is filtered off and washed with diethyl ether. The title compound is thus obtained with an m.p. of 195°–196° C.

(c) 1,5-Dimethyl-3-tert-butyl-3-azabicyclo[3.1.1]heptane-2,4-dione

A solution of 52.2 g of 2,6-dimethyl-4-tert.butyl-1,6-heptadiene-3,5dione and 0.5 g of 2,6-di-tert-butyl-p-cresol in 3.9 l of methylene chloride is irradiated for 30 hours analogously to 2b). After concentration, the crude product is chromatographed with toluene-diethyl ether (15:1) on 3 kg of silica gel 60. The title compound is obtained as white crystals of m.p. 65°–65.5° C. (recrystallization from n-pentane at -70° C).

(d) 2,6-Dimethyl-4-tert-butyl-4-aza-1,6-heptadiene-3,5-dione

A solution of 52.7 g of methacrylyl chloride in 570 ml of methylene chloride is added dropwise to a stirred solution, cooled to 0°–5° C., of 71 g of N-tert-butyl-methacrylamide, 50.8 g of triethylamine and 570 ml of methylene chloride. After the addition, the mixture is stirred for 2 ½ hours and the reaction solution is left to stand for 4 days. The concentrated reaction material is taken up in 0.5 l of diethyl ether, the mixture is filtered and the solution is concentrated. The red oil obtained is filtered with hexane-diethyl ether (4:1) on silica gel to give the title compound as a white crystalline product (m.p. 47°–48° C).

USE EXAMPLE 0.1 mol of 3-[6-endo(p-chlorophenyl)-3-azabicyclo[3.1.1]-hept-3-yl]propionic acid hydrochloride are heated under reflux at 100° C. with 13.4 ml of 85% phosphoric acid and 50 ml of chlorobenzene, while stirring. 27 ml of phosphorus trichloride are then added dropwise at 100° C., whereupon evolution of gas takes place. The reaction mixture deposits a thick mass in the course of 30 minutes. The mixture is heated at 100° C. for a further 3 hours and the supernatant chlorobenzene is then decanted off. The viscous mass which remains is heated under reflux at the boiling point with 100 ml of 9 N hydrochloric acid for 3 hours, while stirring. The mixture is filtered hot, with the addition of charcoal, and the filtrate is diluted with acetone, whereupon 3-[6-endo(p-chloro- phenyl)-3-azabicyclo-[3.1.1]-hept-3-yl]-1-hydroxy-propane-1,1-diphosphonic acid separates out; m.p. 224° C. (decomposition).

Tablets containing 75 mg of the active ingredient or a salt thereof, for example the sodium salt, can be produced as follows:

| Constituents (for 1,000 tablets) | |
|---|---|
| Active ingredient | 75.0 g |
| Lactose | 268.5 g |
| Maize starch | 22.5 g |
| Polyethylene glycol 6000 | 5.0 g |
| Talc | 15.0 g |

-continued

| Constituents (for 1,000 tablets) | |
| --- | --- |
| Magnesium stearate | 4.0 g |
| Demineralized water | q.s. |

Production: The solid ingredients are first forced through a sieve of 0.6 mm mesh width. The active ingredient, lactose, talc, magnesium stearate and half the starch are then intimately mixed. The other half of the starch is suspended in 65 ml of water and this suspension is added to a boiling solution of the polyethylene glycol in 260 ml of water. The resulting paste is added to the pulverulent substances and all the components are mixed and granulated, if necessary with the addition of water. The granules are dried overnight at 35° C., passed through a sieve of 1.2 mm mesh width and pressed to biconcave tablets of about 10 mm diameter with a breaking curve on the top surface.

What is claimed is:

1. A compound of the formula I

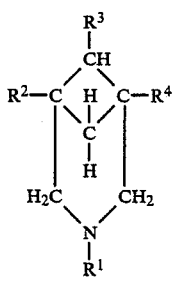

(I)

or an ammonium salt thereof, in which $R^1$ is a hydrogen atom, linear or branched $C_1$–$C_{20}$alkyl, $C_3$–$C_8$cycloalkyl, $C_4$–$C_{20}$alkylcycloalkyl, $C_4$–$C_{12}$ cycloalkylalkyl, $C_5$–$C_{20}$alkylcycloalkylalkyl, $C_6$–$C_{14}$aryl, $C_7$–$C_{20}$alkaryl or aralkyl or $C_8$–$C_{20}$alkaralkyl, which is unsubstituted or substituted by halogen, —OH, —CN, —NO$_2$, $C_1$–$C_6$-halogenoalkyl, —COOH, —SO$_3$H, $R^5$CO-, $R^5$COO-, $R^5$OCO-, $R^5$OSO$_2$-, $R^5$SO$_2$-, $R^5$SO$_3$-, $C_1$–$C_6$-halogenoalkyl, $C_1$–$C_6$alkoxy, $C_1$–$C_6$alkylthio, $C_6$–$C_{10}$ aryloxy or arylthio or $C_7$–$C_{12}$aralkyloxy or aralkylthio, in which $R^5$ is $C_1$–$C_{12}$alkyl, $C_4$–$C_7$cycloalkyl, $C_5$–$C_{16}$alkylcycloalkyl or cycloalkylalkyl, $C_6$–$C_{16}$alkylcycloalkylalkyl, $C_6$–$C_{10}$aryl, $C_7$–$C_{16}$aralkyl or alkaryl or $C_8$–$C_{16}$alkaralkyl, $R^2$ is a hydrogen atom, linear or branched $C_1$–$C_{20}$alkyl, alkoxy, alkylthio, $C_3$–$C_8$cycloalkyl, $C_4$–$C_{20}$alkylcycloalkyl or cycloalkylalkyl, $C_5$–$C_{20}$alkylcycloalkylalkyl, $C_3$–$C_8$cycloalkyloxy or -thio, $C_4$–$C_{20}$alkylcycloalkyloxy or -thio or cycloalkylalkyloxy or -thio, $C_5$–$C_{20}$alkylcycloalkylalkyloxy or -thio, $C_6$–$C_{14}$aryl, aryloxy or arylthio, $C_7$–$C_{20}$alkaryl, alkaryloxy or alkarylthio, $C_7$–$C_{20}$aralkyl, $C_7$–$C_{20}$aralkyloxy or -thio, $C_8$–$C_{20}$alkaralkyl or $C_8$–$C_{20}$alkaralkyloxy or -thio, which is unsubstituted or is substituted as defined for $R^1$, $R^4$ independently has the same meaning as $R^2$, with the exception of $C_6$–$C_{14}$aryl and $C_7$–$C_{20}$alkaryl which is unsubstituted or substituted as defined for $R^1$, and $R^3$ independently has the meaning of $R^2$, or is halogen, carboxyl or carboxylate having 2 to 16 C atoms, with the proviso that $R^1$, $R^2$, $R^3$ and $R^4$ are not simultaneously H.

2. A compound according to claim 1, in which $R^1$ is a hydrogen atom or unsubstituted or substituted $C_1$–$C_{12}$alkyl, $C_5$–$C_7$cycloalkyl, $C_6$–$C_{16}$ alkylcycloalkyl or -cycloalkylalkyl, $C_7$–$C_{16}$alkylcycloalkylalkyl, $C_6$–$C_{10}$aryl, $C_7$–$C_{16}$aralkyl or -alkaryl or $C_8$–$C_{16}$alkaralkyl.

3. A compound according to claim 1, in which $R^1$ is a hydrogen atom or unsubstituted or substituted $C_1$–$C_6$alkyl, cyclopentyl, cyclohexyl, $C_1$–$C_4$alkylcyclopentyl or -cyclohexyl, cyclopentyl—$C_nH_{2n}$- or cyclohexyl—$C_nH_{2n}$-, $C_1$–$C_4$alkylcyclopentyl-$C_nH_{2n}$- or $C_1$–$C_4$alkylcyclohexyl—$C_nH_{2n}$-, phenyl, $C_1$–$C_4$alkylphenyl, phenyl—$C_nH_{2n}$- or $C_1$–$C_4$alkylphenyl-$C_nH_{2n}$-, which n is a number from 1 to 4.

4. A compound according to claim 1, in which $R^1$ is H, unsubstituted or substituted $C_1$–$C_6$alkyl, phenyl or benzyl.

5. A compound according to claim 1, in which $R^2$ is H or unsubstituted or substituted $C_1$–$C_{12}$alkyl, -alkoxy or -alkylthio, $C_5$–$C_7$cycloalkyl, $C_6$–$C_{16}$alkylcycloalkyl or -cycloalkylalkyl, $C_7$–$C_{16}$alkylcycloalkylalkyl, $C_5$–$C_7$cycloalkoxy or -thio, $C_6$–$C_{16}$alkylcycloalkyloxy or -thio or -cycloalkylalkyloxy or -thio, $C_7$–$C_{16}$alkylcycloalkylalkyloxy or -thio, $C_6$–$C_{10}$aryl, -aryloxy or -arylthio, $C_7$–$C_{16}$alkaryl, -alkaryloxy or -thio or -aralkyloxy or -thio, $C_8$–$C_{16}$alkaralkyloxy or -thio, $C_7$–$C_{16}$alkaryl or $C_8$–$C_{16}$alkaralkyl.

6. A compound according to claim 1, in which $R_2$ is a hydrogen atom or unsubstituted or substituted $C_1$–$C_6$alkyl, phenyl or $C_1$–$C_4$alkylphenyl.

7. A compound according to claim 1, in which $R^2$ is H, $C_1$–$C_4$alkyl, unsubstituted or substituted phenyl or $C_1$–$C_4$alkylphenyl.

8. A compound according to claim 1, in which $R^4$ is H or $C_1$–$C_6$ alkyl.

9. A compound according to claim 1, in which $R^3$ is H or unsubstituted or substituted $C_1$–$C_{12}$alkyl, -alkoxy or -alkylthio, $C_5$–$C_7$cycloalkyl, $C_6$–$C_{16}$alkylcycloalkyl or -cycloalkylalkyl, $C_7$–$C_{16}$alkylcycloalkylalkyl, $C_5$–$C_7$cycloalkoxy or -thio, $C_6$–$C_{16}$alkylcycloalkyloxy or -thio or -cycloalkylalkyloxy or -thio, $C_7$–$C_{16}$alkylcycloalkylalkyloxy or -thio, $C_6$–$C_{10}$aryl, -aryloxy or -arylthio, $C_7$–$C_{16}$alkaryl, -alkaryloxy or -thio or -aralkyloxy or -thio, $C_8$–$C_{16}$alkaralkyloxy or -thio, $C_7$–$C_{16}$alkaryl or $C_8$–$C_{16}$alkaralkyl, F, Cl, Br, carboxyl or carboxylate having 2 to 8 C atoms.

10. A compound according to claim 1, in which $R^3$ is H, $C_1$–$C_6$alkyl, unsubstituted or substituted phenyl or $C_1$–$C_4$alkylphenyl.

11. A compound according to claim 1, in which $R^4$ is H and $R^2$ is phenyl, or $R^2$ and $R^4$ are methyl and $R^1$ and $R^3$ are H.

* * * * *